United States Patent [19]

Perrone et al.

[11] Patent Number: 4,713,378
[45] Date of Patent: Dec. 15, 1987

[54] PENEM DERIVATIVES

[75] Inventors: Ettore Perrone; Marco Alpegiani; Franco Zarini; Costantino D. Bruna; Giovanni Franceschi, all of Milan, Italy

[73] Assignee: Farmitalia Carlo Erba S.p.A., Milan, Italy

[21] Appl. No.: 747,829

[22] Filed: Jun. 24, 1985

[30] Foreign Application Priority Data

Jun. 29, 1984 [GB] United Kingdom ............... 8416651

[51] Int. Cl.$^4$ .................... C07D 499/00; A61K 31/425
[52] U.S. Cl. ...................................... 514/192; 514/195
[58] Field of Search .................. 260/245.2 R; 540/310, 540/350; 514/210, 192, 195

[56] References Cited

U.S. PATENT DOCUMENTS 4,272,437 6/1981 Menard et al. .................. 544/236
4,536,335 8/1985 Kim et al. .................. 260/265.2 T
4,631,150 12/1986 Battistini et al. .................. 540/310

FOREIGN PATENT DOCUMENTS 0110826 6/1984 European Pat. Off. .

Primary Examiner—Nicholas S. Rizzo
Attorney, Agent, or Firm—Wegner & Bretschneider

[57] ABSTRACT

There are provided compounds of formula

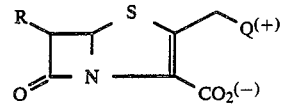

wherein R is hydrogen atom or $C_1$–$C_3$ alkyl group optionally substituted from halogen atom or hydroxy group optionally protected, and $Q^{(+)}$ represents a group

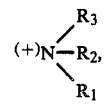

wherein $R_1$, $R_2$ and $R_3$ are each either:
(i) optionally substituted alkyl, aralkyl or aryl radical or
(ii) $R_1$ is as defined above under (i) and $R_2$, $R_3$, taken together, represent an optionally substituted or fused heterocyclic radical or
(iii) $R_1$, $R_2$, $R_3$, taken together, represent an optionally substituted azonia-bicyclo or tricyclo radical or
(iv) $R_1$, $R_2$, $R_3$, taken together, represent an optionally substituted fused pyridinium radical or
(v) $R_1$, $R_2$, $R_3$, taken together, represent an optionally substituted pyrazimium, pyrazolium or pyridazinium radical, and the pharmaceutically or veterinarily acceptable salts thereof.

A method of preparation is also provided.

The compounds show high antibacterial activity.

14 Claims, No Drawings

PENEM DERIVATIVES

The present invention relates to new penem compounds, to a process for their preparation, and to pharmaceutical and veterinary compositions containing them. Compounds of the invention are penem derivatives of the following formula (I)

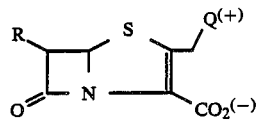 (I)

wherein
R is hydrogen or a $C_1-C_3$ alkyl group either unsubstituted or substituted by one or more substituents chosen from a free or protected hydroxy and halogen atom;
$Q^{(+)}$ represents a group

wherein $R_1$, $R_2$ and $R_3$ are either
(i) each independently an optionally substituted alkyl, aralkyl or aryl radical; or
(ii) $R_1$ is as defined above under (i) and $R_2$, $R_3$ taken together with the nitrogen atom represent an optionally substituted heterocyclic or fused heterocyclic radical; or
(iii) $R_1$, $R_2$, $R_3$, taken together with the nitrogen atom, represent an optionally substituted azoniabicyclo or azoniatricyclo radical; or
(iv) $R_1$, $R_2$, $R_3$, taken together with the nitrogen atom, represent a pyridinium radical to which one phenyl ring or a 5-7 membered, saturated or unsaturated cycloaliphatic or heterocyclic ring is fused, the pyridinium radical and/or the ring fused to it optionally being substituted; or
(v) $R_1$, $R_2$, $R_3$, taken together with the nitrogen atom, represent an optionally substituted pyrazinium, pyrazolium, or pyridazinium radical; and the pharmaceutically or veterinarily acceptable salts thereof.

The present invention includes all the possible geometrical and optical isomers of the compounds of formula (I), either in the form of isomeric mixtures or in the form of the individual separated isomers. Preferably, the compounds of formula (I) have a (5R,6S) configuration. The preferred R group is an (α-hydroxy)ethyl radical and this radical preferably has a (1R) configuration, i.e. a R configuration at the α-carbon atom of the ethyl group.

As already said also the pharmaceutically or veterinarily acceptable salts of the compounds of formula (I) are included within the scope of the invention. The said salts may be both salts with acids, either inorganic acids such as, e.g., acetic, citric, tartaric, fumaric or methanesulphonic acid, and salts with bases, either inorganic bases such as, e.g., alkali or alkaline-earth metal hydroxides, in particular sodium and potassium hydroxides, or organic bases such as, e.g., triethylamine, pyridine, benzylamine or collidine, including aminoacids such as, e.g., lysine or procaine. The invention includes also inner salts, i.e. zwitterions. The alkyl groups, including the aliphatic moieties of the alkoxy, alkylthio and alkanoyl groups, may be branched or straight chain. Preferably, the alkyl and aralkyl radicals under definition (i) for Q are optionally substituted $C_1-C_4$ alkyl and $C_7-C_{11}$ aralkyl radicals. In the definitions of $R_1$, $R_2$ and $R_3$, the substituents for the mentioned alkyl, aralkyl, aryl, heterocyclic, azoniabicyclo, azoniatricyclo, fused pyridinium, pyrazinium, pyrazolium and pyridazinium radicals are preferably selected from the group consisting of: (a) halogen; (b) hydroxy; (c) $C_1-C_4$ alkoxy; (d) $C_1-C_4$ alkylthio; (e) a group

wherein each of $R_4$ and $R_5$ is, independently, hydrogen or $C_1-C_4$ alkyl; (f) sulfo; (g) $-CO_2R_4$ wherein $R_4$ is as defined above; (h) $-C\equiv N$; (i) dimethylformimidino; (j) a group

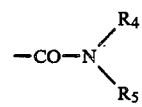

wherein $R_4$ and $R_5$ are as defined above; (k) carbamoyloxy; (l) a hydroxyminomethyl (HO—N=CH—) or methoxyminomethyl ($CH_3O$—N=CH—) group; (m) a formamido or acetamido group; (n) a formyloxy or acetoxy group; (o) a $C_1-C_4$ alkanoyl group; (p) an aryl group; (q) a saturated or unsaturated heterocyclic ring; (r) a nitro group; (s) a mesyloxy group; (t) an oxo group; and (u) a $C_1-C_4$ alkyl group either unsubstituted or substituted by a substituent chosen from (a) to (t) above.

In the present specification, the term "halogen" preferably encompasses fluorine and chlorine atoms, but also iodine and bromine atoms.

The term "aryl" encompasses, preferably phenyl and naphthyl groups. The heterocyclic rings may be saturated or unsaturated, may have from 4 to 7 members and may contain from 1 to 4 heteroatoms selected from oxygen, nitrogen and sulphur atoms.

A $C_1-C_4$ alkyl group is, preferably, methyl or ethyl.

A $C_1-C_4$ alkoxy group is, preferably, methoxy or ethoxy.

A $C_1-C_4$ alkylthio group is, preferably, methylthio or ethylthio.

A $C_1-C_4$ alkanoyl group is, preferably, acetyl or propionyl.

A protected hydroxy group may be a hydroxy group protected by a protecting group chosen, for instance, from an optionally substituted, especially halo-substituted, acyl group, e.g., acetyl, monochloroacetyl, dichloroacetyl, trifluoroacetyl, benzoyl or p-bromophenacyl; a triarylmethyl group, in particular triphenylmethyl; a silyl group, in particular trimethylsilyl, dimethyl-tert-butylsilyl, diphenyl-tert-butyl silyl; or also a group such as tert-butoxy carbonyl, p-nitrobenzyloxycarbonyl, 2,2,2,-trichloroethoxycarbonyl, allyloxycarbonyl, benzyl, and pyranyl. Preferred protecting groups of the hydroxy function are p-nitrobenzyloxycarbonyl; dimethyl-tert-butyl-silyl; diphenyl-tert-butyl-silyl; trimethyl silyl; allyloxycarbonyl; benzyl; p-bromo-phenacyl; triphenylmethyl and pyranyl.

A preferred class of compounds under this invention includes compounds of formula (I) wherein R is an (α-hydroxy)ethyl group and either:

(i') $R_1$, $R_2$, $R_3$ are each independently methyl, ethyl, n-propyl, i-propyl, dimethylaminomethyl, cyanomethyl, cyanoethyl, carbamoylmethyl, 2-hydroxyethyl, 2-chloroethyl, carboxymethyl, ethoxycarbonylmethyl, carboxyethyl, 2-methyl-2-cyanoethyl, 3-oxobutyl or dimethylformimidino group

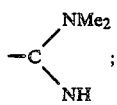

or (ii') $R_1$ is as defined above under (i'), still preferably methyl, ethyl, chloroethyl, cyanomethyl, cyanoethyl, hydroxyethyl or aminoethyl, and $R_2$, $R_3$, taken together with the nitrogen atom, represent one of the following heterocyclyl ammonium radicals

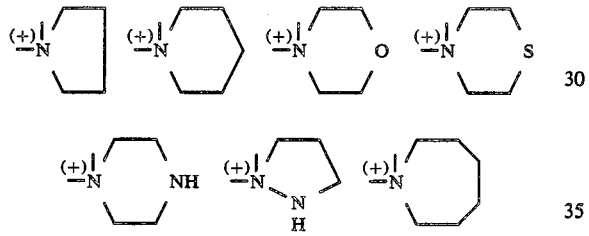

said rings when fused with a second aliphatic, aromatic or heterocyclic ring, are preferably forming one of the following ammonium radicals

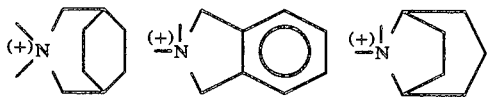

in said heterocyclic ring, when substituted, the substituents being one or more, preferably one or two, equal or different and seleted from the group (a), (b),(e), (g), (h), (i), (q), (t) and (u) as defined above; or (iii') $R_1$, $R_2$, $R_3$, taken together with the nitrogen atom, represent one of the following radicals

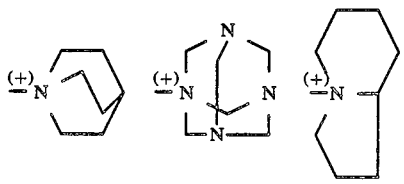

wherein the quinuclidine ring may be substituted by an oxo or hydroxy or methoxy group; or (iv') $R_1$, $R_2$, $R_3$, taken together with the nitrogen atom, represent one of the following fused pyridinium radicals

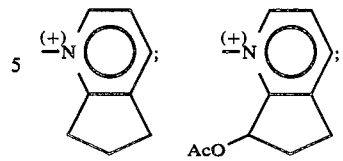

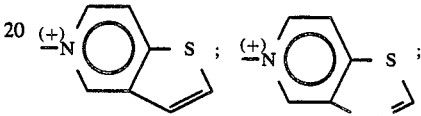

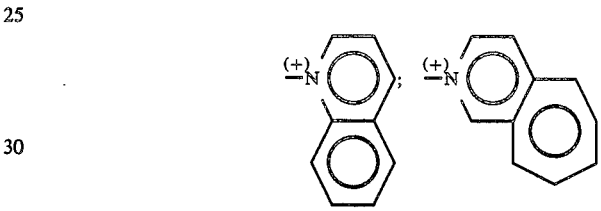

(v') $R_1$, $R_2$, $R_3$, taken together with the nitrogen atom, represent one of the following radicals

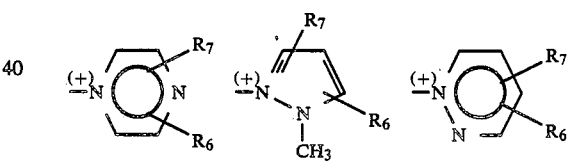

wherein $R_6$, $R_7$ are each independently hydrogen atom, $C_1$–$C_4$ alkyl, or cyanomethyl, and the pharmaceutically or veterinarily acceptable salts thereof. Specific examples of preferred compounds of the invention are those listed in the following table

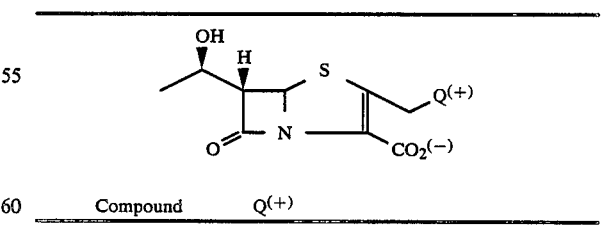

Compound    $Q^{(+)}$

1

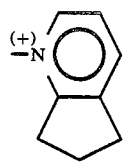

5
-continued
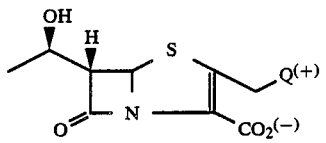
| Compound | Q(+) |
|---|---|
| 2 | 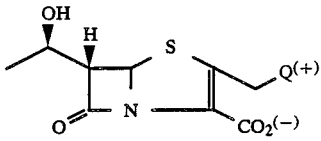 |
| 3 | $\overset{(+)}{-}N(CH_2CH_3)_3$ |
| 4 | $\overset{(+)}{-}N(CH_3)_3$ |
| 5 | 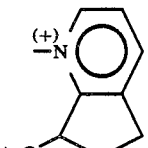 |
| 6 |  |
| 7 |  |
| 8 | 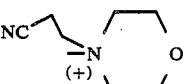 |
| 9 | $\underset{(+)}{-}N(CH_3)_2CH_2CH_2CO_2H$ |
| 10 | $\underset{(+)}{-}N(CH_3)_2CH_2CH_2Cl$ |
| 11 | $\underset{(+)}{-}N(CH_3)_2CH_2CH_2OH$ |
| 12 |  |
| 13 | $\underset{(+)}{-}N(CH_2CH_3)_2CH_2CN$ |
| 14 | $\underset{(+)}{-}N(CH_2CN)_2CH_2CH_3$ |
| 15 | $\underset{(+)}{-}N(CH_2CH_3)_2CH_2CONH_2$ |
| 16 | 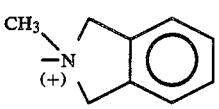 |
6
-continued
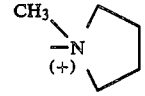
| Compound | Q(+) |
|---|---|
| 17 | 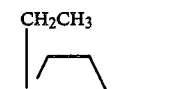 |
| 18 | 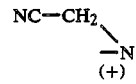 |
| 19 |  |
| 20 | 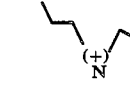 |
| 21 | 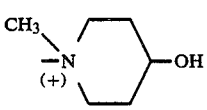 |
| 22 | 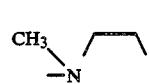 |
| 23 | 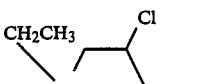 |
| 24 | 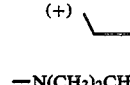 |
| 25 | 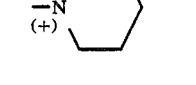 |
| 26 | 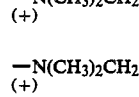 |
| 27 | 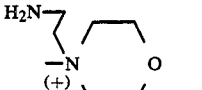 |

-continued
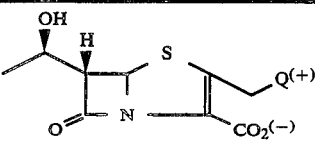
| Compound | Q(+) |
|---|---|
| 28 | 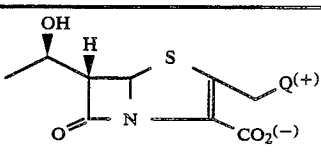 |
| 29 |  |
| 30 |  |
| 31 | 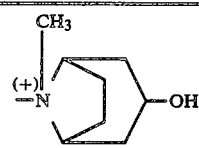 |
| 32 | 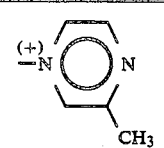 |
| 33 | 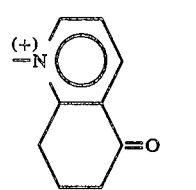 |
| 34 | 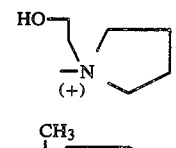 |
| 35 | 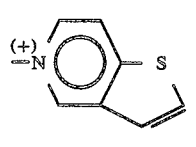 |
| 36 | 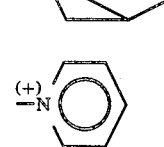 |
| 37 | 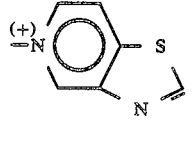 |
-continued
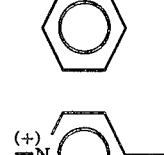
| Compound | Q(+) |
|---|---|
| 38 | 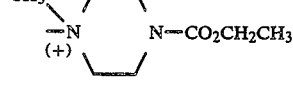 |
| 39 | 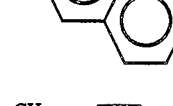 |
| 40 | 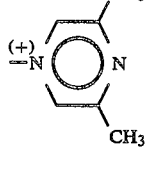 |
| 41 | 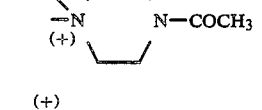 |
| 42 | 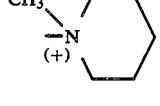 |
| 43 | 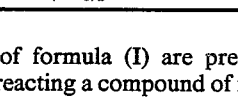 |
| 44 | $-\overset{(+)}{N}(CH_2CH_2CH_2CH_3)_3$ |
| 45 | $-\overset{(+)}{N}(CH_3)_2Ph$ |
The compounds of formula (I) are prepared by a process comprising reacting a compound of formula (II)
$$N \begin{matrix} R_3 \\ -R_2 \\ R_1 \end{matrix} \qquad (II)$$
wherein $R_1$, $R_2$ and $R_3$ are as defined above, either with a penem intermediate of formulla (III)
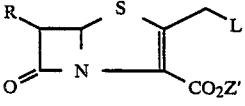 (III)

wherein R is as defined above, Z' is a carboxy protecting group, and L is a leaving group susceptible of nucleophilic displacement by the reagent (II), or with a 2-thiacephem derivative of formula (IV)

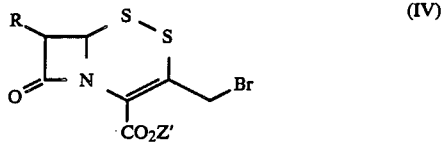

wherein R is as defined above and Z' is a carboxy protecting group, and, where necessary or desired, removing the protecting groups possibly present in the product of the reaction between the compound (II) and the compound (III) or, in any order, desulphurizing the product of the reaction between the compound (II) and the compound (IV) and removing the protecting groups therein present, and, if desired, converting an obtained compound into a salt thereof and/or, if desired, separating a mixture of isomers into the single isomers.

The leaving group L in the compound, of formula (III) may be, for example, a sulphonyloxy group, preferably trifluoromethanesulphonyloxy ($-O-SO_2CF_3$), or a halogen atom, preferably chlorine, bromine or iodine.

A carboxy protecting group Z' may be any group which, together with the $-CO_2-$ moiety, forms an esterified carboxy group. Examples of carboxy protecting groups are, in particular, $C_1-C_6$ alkyl groups, for instance methyl, ethyl or tert-butyl; halo-substituted $C_1-C_6$ alkyl groups, for example 2,2,2-trichloroethyl; $C_2-C_4$ alkenyl groups, for example allyl; optionally substituted aryl groups, for example phenyl and p-nitrophenyl; optionally substituted aryl-$C_1-C_6$ alkyl groups, for example benzyl, p-nitro-benzyl and p-methoxy-benzyl; aryloxy-$C_1-C_6$ alkyl groups, for example phenoxymethyl; or groups such as benzhydryl, o-nitro-benzyhydryl, acetonyl, trimethylsilyl, diphenyl-tert-butyl-silyl, and dimethyl-tert-butyl-silyl, or groups such as pivaloyloxy methyl or phthalidyl.

Particularly preferred carboxy protecting groups are allyl, p-nitrobenzyl, trimethylsilyl, dimethyl-tert-butyl-silyl, and trichloroethyl.

When in the compound of formula (IV) R is a $C_1-C_3$ alkyl group substituted by hydroxy, the hydroxy is preferably protected, and a particularly preferred protecting group is dimethyl-tert-butyl-silyl.

The reaction between a compound of formula (II) and a compound of formula (III), may be performed in a suitable organic, preferably aprotic, solvent which may be, for instance, tetrahydrofuran, dimethylformamide, acetone or a halogenated hydrocarbon such as, e.g.,dichloromethane. The reaction temperature may, preferably, vary between about $-70°$ C. and about $+25°$ C., preferably between $-40°$ C. and $+15°$ C. A compound of formula (III) wherein L is a sulphonyloxy group may be prepared reacting, according to known and conventional procedures, a hydroxymethyl penem precursor of formula (V)

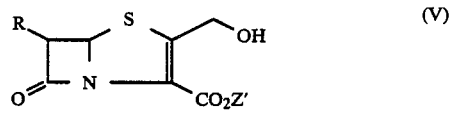

wherein R and Z' are as defined above, with the appropriate sulphonyl anhydride or sulphonyl halide, preferably triflic anhydride, a triflic chloride, in the presence of a non-nucleophilic acid acceptor which may be, for instance, an inorganic base such as, e.g., calcium or lithium carbonate or calcium oxide, or an organic base such as, e.g., 2,6-lutidine or also the same compound of formula (II) to be reacted in the subsequent step. Indeed, according to a preferred procedure of the invention the compound of formula (V) is made to react with the suitable sulphonyl anhydride or sulphonyl halide in the presence of an excess, usually an amount equal to or greater than 2 molar equivalents, of the desired compound of formula (II): in this situation the compound of formula (III) is not even isolated from the reaction mixture because it reacts in situ with the compound of formula (II).

The hereabove said preferred procedure is preferably carried out using dry dichloromethane as solvent at temperatures from about $-40°$ C. to about $0°$ C. When a compound of formula (II) is reacted with a compound of formula (III) wherein L is halogen, particularly chlorine, the presence of a silver salt soluble in the media, e.g. $AgClO_4$, may be beneficial.

A compound of formula (III) wherein L is halogen, in particular chlorine, may be prepared from the corresponding hydroxymethyl penem precursor of formula (V) according to a modified Mitsunobu reaction in which the carbinol of formula (V) is allowed to react with an organic amine hydrohalide, preferably an organic amine hydrochloride such as, for instance, methoxyamine hydrochloride or pyridine hydrochloride, and the preformed complex obtained from diethylazodicarboxylate and triphenylphosphine, the said reaction being carried out, e.g., in tetrahydrofuran or methylene chloride, preferably at room temperature.

With particularly inert compounds of formula (II) it may be preferable to perform the displacement reaction on a 2-thia-cephem compound of formula (IV) rather than on a penem derivative of formula (III). The reaction is then carried out in an inert organic solvent, such as, for instance, dichloromethane, tetrahydrofuran, dimethylsulphoxide or dimethylacetamide, and optionally in the presence of a iodide salt, e.g. NaI, or with a silver salt, e.g. $AgClO_4$, at temperature ranging from about $-15°$ C. to about $+50°$ C., to obtain a 2-thiacephem intermediate of formula (VI)

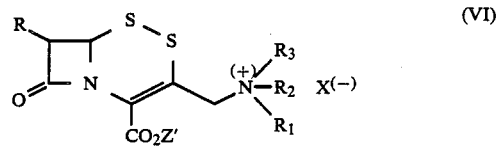

wherein R, $R_1$, $R_2$, $R_3$ and Z' are as defined above, and $X^{(-)}$ is a counterion, such as, e.g., depending on the reaction and work-up conditions, $Br^{(-)}$, $I^{(-)}$, $ClO_4^{(-)}$, $(-)OCOCH_3$, and such compound of formula (VI) is then, in any order, desulphurized and deprotected to obtain the desired compound of formula (I).

A suitable desulphurizing agent is triphenylphosphine: see, for example, E. Perrone et al, Tetrahedron Lett., 24, 1631 (1983). Other desulphuration conditions, which can be applied on 2-thiacephems of formula (VI) to give, after removal of the protecting group in Z', penems of formula (I), are object of our UK Patent Application No. 2,131,432 A, published on June 6, 1984.

Removal of the protecting groups can be effected by known per se procedures; e.g. silyl groups can be removed under mild acidic conditions, or by fluoride ions, e.g. with tetrabutylammonium fluoride; p-nitrobenzyl groups can be removed by reduction, e.g. by catalytic hydrogenation, or with metals, such as Fe and Zn; allyl carboxylates can be cleaved by transallylation with an organic acid or a salt thereof, such as acetic acid, 2-ethylhexanoic acid or their sodium and potassium salts, this reaction being catalyzed by a triphenylphosphine-palladium complex, preferably by tetrakis-triphenylphosphine-Pd°. The optional salification of an obtained compound and the separation of a mixture of isomers into the single isomers may be carried out following known and conventional procedures.

The amines of formula (II) are known compounds, or can be prepared from known compounds by known methods. Intermediates of formula (V) have been described in our UK Patent Application No. 2,111,496; intermediates of formula (IV) have been described in our UK Patent application No. 2,131,432 A. The compounds of formula (I) provided by the present invention are potent, broad spectrum antibacterial agents. The following table shows the activity of a typical compound of formula (I), the Compound 5 of the previous table.

Comparison between the antibacterial in vitro activity (MIC, µg/ml) of compound "5" and two reference drugs: FCE 21420 and Cefotaxime

| Organism | Compound "5" | FCE 21420 | Cefotaxime |
| --- | --- | --- | --- |
| Staphylococcus aureus Smith | <<0.005 | 0.023 | 0.78 |
| Staphylococcus aureus 209 P | <<0.005 | 0.045 | 1.56 |
| Streptococcus pyogenes ATCC 12384 | <<0.005 | 0.045 | 0.78 |
| Klebsiella aerogenes 1082E (β-lact.+) | 0.045 | 0.78 | 3.12 |
| Enterobacter cloacae 1321 E | 0.045 | — | — |
| Enterobacter cloacae P 99 (β-lact.+) | 0.045 | 3.12 | >100 |
| Escherichia coli B | 0.045 | 0.39 | 0.011 |
| Escherichia coli B Cef. R (β-lact.+) | 0.045 | 0.39 | 0.19 |
| Escherichia coli 026:B6 | 0.005 | 0.39 | 0.78 |
| Escherichia coli 026:B6 Cef R | 0.045 | 3.12 | 1.56 |
| Salmonella typhimurium ATCC 14028 | 0.045 | 0.39 | 0.045 |
| Shigella flexneri ATCC 11836 | 0.045 | 0.39 | 0.023 |
| Proteus mirabilis FI 7474 | 0.19 | — | — |
| Proteus morganii ATCC 25830 | 0.38 | 0.78 | 0.011 |
| Citrobacter freundii ATCC 8090 | 0.09 | 0.78 | — |
| Pseudomonas aeruginosa ATCC 19660 | 25 | >50 | 12 |
| Serratia marcescens ATCC 2902 | 0.78 | 3.1 | — |

Compound "5" = (5R,6S)-6-[(1R)-hydroxyethyl]-2-[1-(1-methylpyrrolidinio)]-methylpenem-3-carboxylate, prepared in example 2.
FCE 21420 = sodium (5R,6S)-6-[(1R)-hydroxyethyl]-2-acetoxy methyl-penem-3-carboxylate (see A. Sanfilippo et al., J. Antibiotics 35, 1248 (1982)).

Moreover, it has been found that the compounds of formula (I) of the present invention are scarcely bound to the serum proteins.

A number of them are remarkably active against Pseudomonas aeruginosa strains. When tested in vivo after parental administration, these compounds showed a very high degree of therapeutic effectiveness in treating infections caused by both Gram-positive and Gram-negative bacteria, their toxicity being on the other hand quite negligible.

Owing to their high antibacterial activity the compounds of the invention are thus useful, for example, in the treatment of respiratory tract infections, for example, bronchitis, bronchopneumonia, pleurisy; hepatobiliary and abdominal infections, for example, septicemia; urinary tract infections, for example, pyelonephritis, cystitis; obstetrical and gynecological infections, for instance, cervicitis, endometritis; ear, nose and throat infections, for instance otitis, sinusitis, parotitis.

The compounds of the invention may be administered, either to humans or to animals, in a variety of dosage forms, e.g., orally in the form of tablets, capsules, drops or syrups; rectally in the form of suppositories; parenterally, e.g., intravenously or intramuscularly (as solutions or suspensions), with intravenous administration being preferred in emergency situation; by inhalation in the form of areosols or solutions for nebulizers; intravaginally in the form, e.g., of bougies; or topically in the form of lotions, creams and ointments. The pharmaceutical or veterinary compositions containing the compounds of formula (I), which are too within the scope of the invention, may be prepared in a conventional way by employing the conventional carriers or diluents used for, e.g., cephalosporins.

Conventional carriers or diluents are, for example, water, gelatine, lactose, starches, magnesium stearate, talc, vegetable oils, cellulose and the like. Daily doses in the range of about 0.5 to about 100 mg per kg of body weight may be used, in various animal species, the exact dose depending on the age, weight and condition of the subject to be treated and on the frequency and route of administration.

A preferred way of administration of the compounds of the invention is the parenteral one: in this case the compounds may be administered, for example to adult humans, in an amount ranging from about 250 mg to about 1000 mg pro dose, preferably about 500 mg pro dose, 1–4 times a day, dissolved in a suitable solvent, such as, for example, sterile water or lidocaine hydrochloride solution for intramuscolar injections, and sterile water, physiological saline solution, dextrose solution or the conventional intravenous fluids or electrolytes, for intravenous injections. Furthermore, the compounds of the invention may be used as antibacterial agents in a prophylactic manner, e.g., in cleaning or as surface disinfecting compositions, for example, at a concentration of about 0.2 to 1% by weight of such compounds admixed with, suspended or dissolved in conventional inert dry or aqueous carriers for application by washing or spraying.

They are also useful as nutritional supplements in animal feeds.

The following examples illustrate but do not limit the present invention.

EXAMPLE 1

(5R,6S)-6-[(1R)-hydroxyethyl]-2-[1-(6,7-dihydro-5H-cyclopenta[b]pyridinio]-methylpenem-3-carboxylate (1)

A solution of p-nitrobenzyl-(5R,6S)-6-[(1R)-p-nitrobenzyloxycarbonyloxyethyl]-2-hydroxymethyl-penem-3-carboxylate (600 mg) in dry,ethanol free, dichloromethane (10 ml) was cooled under nitrogen to −40° C. and then sequentially treated under stirring with 6,7-dihydro-5H-cyclopenta[b]pyridine (0.9 ml) and trifluoromethanesulphonic anhydride (0.35 ml). The reaction mixture was let rise to −5° C. and then quenched with 0.1 M aqueous HCl. The organic layer was separated, washed with brine, dried and evaporated, to give a gummy residue which was triturated in ethyl acetate-ethyl ether mixtures. The solid was dissolved in a minimum amount of chloroform and added to a well-stirred solution of ethyl ether, thus obtaining the bis-protected precursor of the tile compound as a white-off powder; 0.5 g; νmax (film) 1795, 1750, 1715 cm⁻¹. This product was dissolved in tetrahydrofuran (40 ml) and this solution was mixed with a solution of NH₄Cl (10 g) in water (40 ml), and the whole was vigorously stirred with iron powder (5 g) at 10° C.-15° C. The reaction was monitored by TLC (H₂O—MeOH—NaCl 9:1:1); it was usually over within 45-90 minutes.

The mixture was filtered through a short bed of Celite 521, thoroughly washed with 15% tetrahydrofuran in water, and then freed from the organic solvent by evaporation in vacuo at ≦15° C. The aqueous solution was washed with ethyl acetate, concentrated to a small volume and passed through a reverse-phase column (Lichroprep RP-18 Merck) eluting first with demineralized water, then with a gradient (0→10%) in acetonitrile. The product-containing fractions were concentrated and then freeze-dried to afford (5R,6S)-6-[(1R)-hydroxyethyl]-2-[1-(6,7-dihydro-5H-cyclopenta[b-]pyridinio]-methylpenem-3-carboxylate (80 mg); νmax (KBr) 1775, 1610, 1580 cm⁻¹ (IR); NMR (200 MHz, D₂O: δp.p.m. 1.26 (3H,d,J=6.5 Hz,CH₃CH),

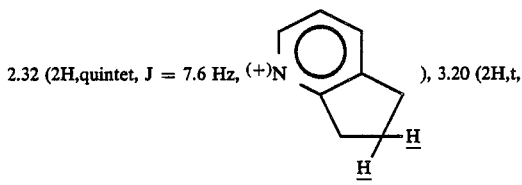
2.32 (2H,quintet, J = 7.6 Hz, ⁽⁺⁾N ), 3.20 (2H,t,

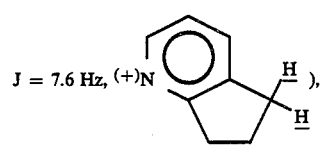
J = 7.6 Hz, ⁽⁺⁾N ),

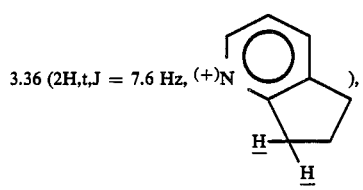
3.36 (2H,t,J = 7.6 Hz, ⁽⁺⁾N ), 3.95 (1H,dd,J=1.6 and 5.9 Hz, H-6), 4.23 (1H,dq,J=5.9 and 6.5 Hz,H-8), 5.67 (1H,d,J=1.6 Hz,H-5), 5.87 (2H,ABq, J=15.6 Hz, CH₂N⁺), 7.78 (1H,dd,J=6.3 and 7.6 Hz,

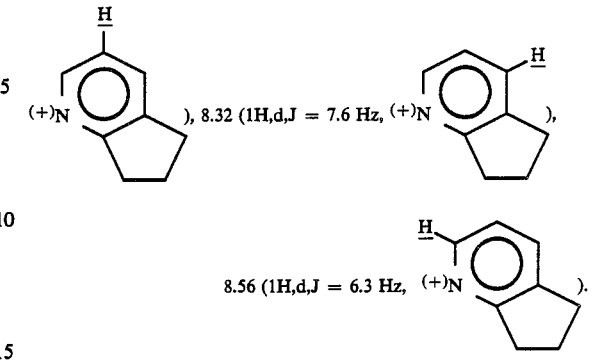

νmax (H₂O) nm(ε) 278 (8,753), 312 (4,312) (UV); TLC (Kieselgel 60 Merck; eluants H₂O-MeOH-NaCl 9:1:1): Rf 0.28.

EXAMPLE 2

(5R,6S)-6-[(1R)-hydroxyethyl]-2-[1-(1-methylpyrrolidinio)]-methylpenem-3-carboxylate (5)

A solution of allyl (5R,6S)-6-[(1R)(-tert-butyldimethylsilyloxyethyl]-2-hydroxymethylpenem-3-carboxylate (500 mg) in dry, ethanol-free dichloromethane (15 ml) was cooled to −50° C. under nitrogen and sequentially treated with 1-methylpyrrolidine (0.66 ml) and trifluoromethane sulphonic anhydride (0.5 ml); TLC showed immediate and complete conversion of the starting material into a new, more polar product. This material, allyl (5R,6S)-6-[(1R)-tert-butyldimethylsilyloxyethyl]-2-[1-(1-methylpyrrolidinio)]-methylpenem-3-carboxylate, triflate salt, was isolated crude after quenching with water, washing with 4% aqueous HCl, and evaporation of the organic layer. The bis-protected intermediate thus obtained was dissolved in dry tetrahydrofuran (20 ml); acetic acid (1.25 ml) and tetrabutylammonium fluoride trihydrate (1.07 g) were added, and the solution was kept for 24 hours in the dark at room temperature. After removal of the solvent, the residue was dissolved in a minimum amount of dichloromethane and chromatographed on SiO₂ (230-400, Mesh "flash chromatography") with CH₂Cl₂, CH₂CH₂—MeOH 70:30, CH₂Cl₂—MeOH 50:50, neat MeOH, and MeOH—H₂O 35:65, in this sequence, as eluants (TLC monitoring: isopropanol-acetic acid-water 5:1:1, Kieselgel 60 Merck). The desilylated product, allyl (5R,6S)-6-[(1R)-hydroxyethyl]-2-[1-(1-methylpyrrolidinio)-methyl]penem-3-carboxylate, acetate salt, was isolated after evaporation in vacuo of the appropriate fractions; 300 mg. This material (200 mg), dissolved in dichloromethane (5 ml), was treated with acetic acid (0.13 ml), triphenylphosphine (30 mg) and tetrakis (triphenylphosphine)palladium(O). More of the three reactants (HOAc 0.02 ml, PPh₃ 20 mg, Pd(Ph₃)₄ 20 mg) were added (three times at 15 min. intervals), while monitoring the depletion of the starting material by TLC. The reaction mixture was evaporated and the residue was digested in ethyl acetate/ethyl ether (3 times), decanting off the liquors. The undissolved material was taken up in a minimum amount of distilled water and purified by reverse-phase chromatography (LiChroprep RP-18 Merck; eluants water and H₂O-MeCN 9:1→7:3 mixtures).

The product-containing fractions (TLC monitoring; Kieselgel 60 Merck, H₂O-MeOH-NaCl 9:1:1; Rf 0.32)

were combined and freeze-dried, affording 115 mg of the title compound; IR: νmax (KBr) 1775, 1615, 1575 cm⁻¹; NMR (200 MHz, D₂O): δp.p.m.: 1.29 (3H,d,J=6.4 Hz,CH₃CH),

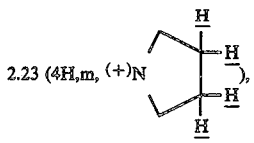

2.23 (4H,m, (+)N ), 3.11 (3H,s,CH₃N+),

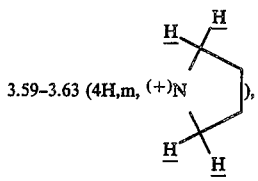

3.59–3.63 (4H,m, (+)N ), 4.03 (1H,dd,J=1.6 and 5.8 Hz, H-6), 4.26 (1H,dq,J=5.8 and 6.4 Hz,H-8), 4.78 (2H,ABq,J=13.8 Hz,CH₂N+), 5.75 (1H,d,J=1.6 Hz,H-5).

UV: λmax (H₂O) nm (ε) 211 (4,674), 256 (2,766) and 316 (4,739).

EXAMPLE 3

(5R,6S)-6-[(1R)-hydroxyethyl]-2-triethylammoniomethylpenem-3-carboxylate (3)

A solution of allyl (5R,6S)-6-[(1R)-tert-butyldimethylsilyloxyethyl]-2-hydroxymethylpenem-3-carboxylate (500 mg) in dry dichloromethane (15 ml) was treated at −50° C. under nitrogen with triethylamine (1.05 ml) and trifluoromethane sulphonic anhydride(0.52 ml). After five minutes, water was added and the stirred mixture let rise to room temperature. The organic layer was separated, washed with 4% aqueous HCl, then with brine, dried and evaporated to give a yellowish powder; νmax (KBr) 1803, 1695, 1565 cm⁻¹ (IR). This material was taken up in tetrahydrofuran (20 ml) and treated in sequence with acetic acid (1.25 ml) and tetrabutylammonium trihydrate (1.07 g). The clear solution was let stand for 16 hours at room temperature, then concentrated and passed through a silica gel column (230–400 Mesh, φ 2 cm, h 12 cm). Elution with neat CH₂Cl₂, CH₂Cl₂/MeOH (70:30 and then 50:50) and neat methanol was followed by final washing with MeOH/H₂O (1:2).

Methanol was removed in vacuo from the last fractions and the allyl ester of the title product (180 mg) was recovered upon addition of NaCl and repeated extractions (10 ×) with dichloromethane. This material (140 mg) in 5 ml of CH₂Cl₂ and 0.1 ml of acetic acid was stirred with triphenylphosphine (0.03 g) and tetrakis(triphenylphosphine)Pd(O) (0.03 g) for 90 min., after which time an additional amount of HOAc (0.025 ml), PPh₃ (0.02 g) and Pd(PPh₃)₄ (0.02 g) was added to complete the reaction (further 15 min.). The reaction mixture was concentrated and the residue triturated with ethyl acetate (3×). The obtained solid was dissolved in demineralized water and chromatographed on LiChroprep RP-18, eluting first with water and then with 20% MeCN in H₂O. The appropriate fractions (TLC on SiO₂, i-PrOH/H₂O/HOAc 5:1:1, Rf 0.16) were combined and freeze-dried to afford 64 mg of the title product as a white powder; IR:νmax (KBr) 1775, 1610, 1570 cm⁻¹; NMR (200 MHz, D₂O): δp.p.m.: 1.29 (3H,d,J=6.5 Hz,CH₃CH), 1.31 (9H,t,J=7.0 Hz, CH₂CH₃), 3.43 (6H,two dq, J=7.0 and 16 Hz,CH₂CH₃), 4.02 (1H,dd, J=5.4 and ≦1.5 Hz,H-6), 4.26 (1H,dq,J=5.4 and 6.5 Hz, H-8), 4.75 (2H,ABq,J=14.5 Hz, CH₂N+), 5.75 (1H,d,J≦1.5 Hz,H-5); UV: λmax (H₂O) nm(ε) 256 (3,406) and 316 (4,637).

EXAMPLE 4

(5R,6S)-6-[(1R)-hydroxyethyl]-2-[4-(4-methylmorpholinio)]methylpenem-3-carboxylate (8)

Allyl (5R,6S)-6-[(1R)-tert-butyldimethylsilyloxyethyl]-2-hydroxymethylpenem-3-carboxylate (500 mg) dissolved in dry dichloromethane (15 ml) was allowed to react at −50° C. under argon with trifluoromethanesulphonic anhydride (0.5 ml) in the presence of 4-methylmorpholine (0.69 ml). After 10 min., the reaction mixture was quenched with water, and the separated organic layer was sequentially washed with 4% aqueous HCl and brine (2X). Evaporation of the solvent left 550 mg of a yellowish syrup which, without further purification, was kept for 20 hours in dry tetrahydrofuran (20 ml) and acetic acid (1.2 ml) in the presence of tetrabutylammonium fluoride trihydrate (1.07 g). Most of the solvent was removed in vacuo and the residue was passed through a silica gel column. After eluting out some by-products and the tetrabutylammonium salts with dichloromethane-methanol mixtures, the column was washed with methanol-water (1:2) to recover the allyl ester of the title product (TLC monitoring; Kieselgel 60 Merck; i-PrOH-AcOH-H₂O 5:1:1; KMnO₄assay); extraction from the MeOH-H₂O liquors could be accomplished by thorough evaporation under high vacuum and trituration of the residue with an ethanoldichloromethane (1:1)mixture. This material, after evaporation of the solvents, was suspended in tetrahydrofuran-dichloromethane (1:1, 10 ml) and treated under stirring for 1 hour with acetic acid (0.15 ml) and PPh₃/Pd(PPh₃)₄ (100 mg each, added in two portions at 30 min.intervals). The reaction mixture was concentrated and partitioned in ethyl acetate-water; the aqueous solution was passed through a LiChroprep RP-18 reverse-phase column, eluting with water and finally with acetonitrile-water, to obtain, upon collection of the appropriate fractions and freeze-drying, 40 mg of the title product; IR: νmax (KBr) 3430, 1770, 1615, 1570 cm⁻¹; NMR (200 MHz, D₂O): δp.p.m.: 1.29 (3H,d,J=6.5 Hz,CH₃CH), 3.28 (3H,s,CH₃N+),

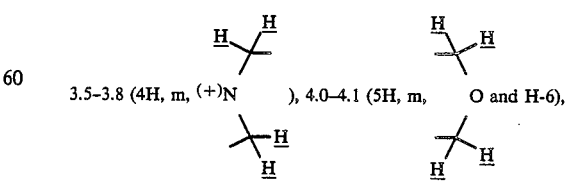

3.5–3.8 (4H, m, (+)N ), 4.0–4.1 (5H, m, O and H-6), 4.26 (1H, dq, dq,J=5.8 and 6.5 Hz,H-8), 4.95 (2H,ABq, J=13.8 Hz,CH₂N+), 5.75 (1H,d,J=1.5 Hz,H-5);

UV: λmax (H₂O) nm(ε) 255 (3,660) and 319 (5,349).

EXAMPLE 5

(5R,6S)-6-[(1R)-hydroxyethyl]-2-[1-(3-oxoquinuclidinio)]methylpenem-3-carboxylate (27)

3-Quinuclidone hydrochloride was converted into the free base by treatment with 20% aqueous NaOH and extraction with dichloromethane, and the obtained syrup (0.78 g) added to a cooled (−40° C.) solution of allyl (5R,6S)-6-[(1R)-tert-butyldimethylsilyloxyethyl]-2-hydroxymethylpenem-3-carboxylate (500 mg) in dichloromethane (15 ml). Trifluoromethanesulphonic anhydride was then added followed after 5 min. by water. The stirred mixture was let rise to room temperature and the organic layer washed with 0.1 M HCl, dried and evaporated to give a foam; $\nu$max(film) 1800, 1755, 1720 cm$^{-1}$. This material, dissolved in tetrahydrofuran (20 ml), was stirred with acetic acid (1.2 ml) and tetrabutylammonium fluoride trihydrate (1.07 g) for 16 hours at room temperature. After removal of the solvent, the residue was poured on the top of a silica gel column, which was eluted in sequence with $CH_2Cl_2$, $CH_2Cl_2$—MeOH, MeOH, MeOH—$H_2O$ (1:2.5). The last fractions were collected and evaporated; the residue was extracted with $CH_2Cl_2$—EtOH (1:1; 2×50 ml)); and the extracts dried over $MgSO_4$, filtered, evaporated, to give a waxy solid (180 mg). Dichloromethane (5 ml) and tetrahydrofuran (2.5 ml) were added, followed by acetic acid (0.15 ml), triphenylphosphine (0.05 g), and tetrakis(triphenylphosphine)palladium(O) (0.05 g); a white precipitate is gradually formed. After 30 min. stirring at room temperature, ethyl ether (5 ml) was added and the crude title compound isolated by centrifugation. Further purification could be achieved by reverse-phase chromatography (water as eluant), thus obtaining 70 mg of pure product;IR:$\nu$max(KBr) 1775, 1745, 1610, 1570 cm$^{-1}$;UV:$\lambda$max($H_2O$) 318 nm ($\epsilon$=4,205).

EXAMPLE 6

Operating as described in the previous examples, the following compounds were analogously prepared:

(5R,6S)-6-[(1R)-hydroxyethyl]-2-[1-(7-acetoxy-6,7-dihydro-5H-cyclopenta[b]pyridinio)]-methylpenem-3-carboxylate(2);

(5R,6S)-6-[(1R)-hydroxyethyl]-2-trimethylammoniomethylpenem-3-carboxylate(4);

(5R,6S)-6-[(1R)-hydroxyethyl]-2-[1-(1-cyanomethylpyrrolidinio)]-methylpenem-3-carboxylate(6);

NMR (200 MHz, $D_2O$)=$\delta$ppm 1.30 (3H, d, J=6.3 Hz),

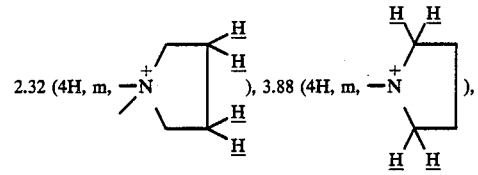

4.08 (1H, dd, J=1.6 and 5.7 Hz, H$_6$), 4.28 (1H, m, H$_8$),

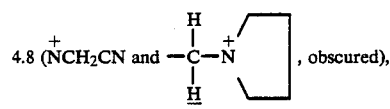, obscured),

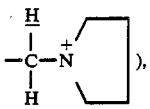

5.80 (1H, d, J=1.6 Hz, H$_5$).

UV ($H_2O$)=$\lambda_{max}$ 321 nm ($\epsilon$=4,626).

TLC (Kieselgel 60 Merck ®; eluants i—PrOH—$H_2O$—HOAc 5:1:1) : Rf 0.19.

(5R,6S)-6-[(1R)-hydroxyethyl]-2-{1-[1-(2-cyanoethyl)-pyrrolidinio]}-methylpenem-3-carboxylate(7);

(5R,6S)-6-[(1R)-hydroxyethyl]-2-(2-carboxyethyl)-dimethylammoniomethylpenem-3-carboxylate(9);

(5R,6S)-6-[(1R)-hydroxyethyl]-2-(2-chloroethyl)-dimethylammoniomethylpenem-3-carboxylate(10);

(5R,6S)-6-[(1R)-hydroxyethyl]-2-(2-hydroxyethyl)-dimethylammoniomethylpenem-3-carboxylate(11);

(5R,6S)-6-[(1R)-hydroxyethyl]-2-[1-(1,1,3,3,-tetramethylguanidinio)]-methylpenem-3-carboxylate(12);

(5R,6S)-6-[(1R)-hydroxyethyl]-2-cyanomethyldiethylammoniomethylpenem-3-carboxylate(13);

(5R-6S)-6-[(1R)-hydroxyethyl]2-dicyanomethylethylammoniomethylpenem-3-carboxylate(14);

(5R,6S)-6-[(1R)-hydroxyethyl]-2-(carbamoylmethyl)-diethylammoniomethylpenem-3-carboxylate(15);

(5R,6S)-6-[(1R)-hydroxyethyl]-2-{1-[1-(2-chloroethyl)-piperidinio]}-methylpenem-3-carboxylate(16);

(5R,6S)-6-[(1R)-hydroxyethyl]-2-[1-(1-methyl-4-oxopiperidinio)]-methylpenem-3-carboxylate(17);

(5R,6S)-6-[(1R)-hydroxyethyl]-2-{4-[4-(2-cyanoethyl)-morpholinio]}-methylpenem-3-carboxylate(18);

(5R,6S)-6-[(1R)-hydroxyethyl]-2-[2-(2-methylisoindolinio)]-methylpenem-3-carboxylate(19);

(5R,6S)-6-[(1R)-hydroxyethyl]-2-[1-(1-ethylpiperidinio)]-methylpenem-3-carboxylate(20);

NMR (200 MHz, $D_2O$): $\delta$ppm 1.32 (3H, d, J=6.3 Hz, $\underline{CH_3}$CH),

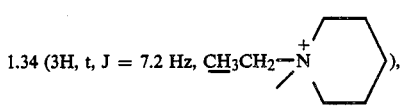

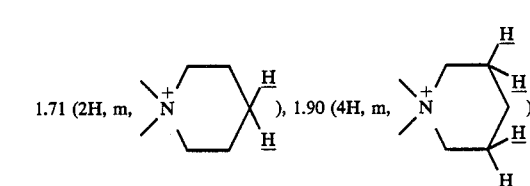

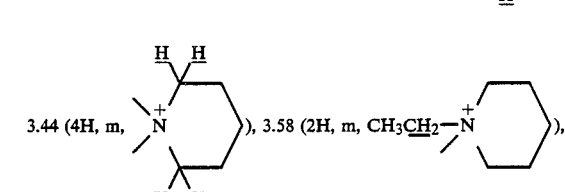

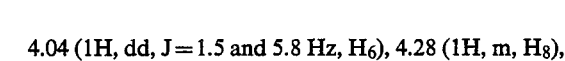

4.04 (1H, dd, J=1.5 and 5.8 Hz, H$_6$), 4.28 (1H, m, H$_8$), 4.36 and 5.20 (2H, each d, J = 14.6 Hz, C$\underline{H}_2$—N 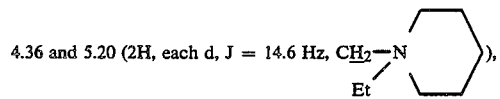), 5.77 (1H, d, J=1.5 Hz, H$_5$).
IR (KBr): $\nu_{max}$ 1775, 1610 cm$^{-1}$
UV (H$_2$O)=$\lambda_{max}$ 213 ($\epsilon$=5,067), 255 ($\epsilon$=3,504), 316 nm ($\epsilon$=4,873).

(5R,6S)-6-[(1R)-hydroxyethyl]-2-[1-(1-methyl-4-hydroxypiperidinio)]-methylpenem-3-carboxylate(21);
(5R,6S)-6-[(1R)-hydroxyethyl]-2-[1-(3-chloro-1-ethyl-piperidinio)]-methylpenem-3-carboxylate(22);
(5R,6S)-6-[(1R)-hydroxyethyl]-2-{4-[4-(2-aminoethyl)-morpholinio]}-methylpenem-3-carboxylate(23);
(5R,6S)-6-[(1R)-hydroxyethyl]-2-[1-(1-methyl-piperazinio)]-methylpenem-3-carboxylate(24);
(5R,6S)-[(1R)-hydroxyethyl]-2-[1-(1,4-dimethyl-piperazinio)]-methylpenem-3-carboxylate(25);
(5R,6S)-6-[(1R)-hydroxyethyl]-2-(1-quinuclidinio)-methylpenem-3-carboxylate(26);
NMR (200 MHz, D$_2$O)=$\delta$ppm 1.32 (3H, d, J=6.4 Hz, C$\underline{H}_3$CH), 2.02 (6H, m, 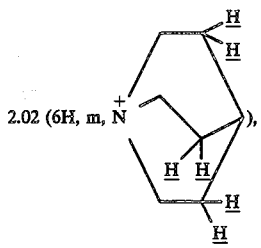), 2.21 (1H, m, 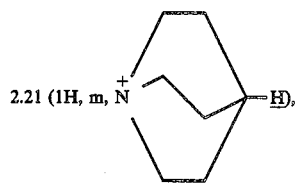), 3.54 (6H, m, 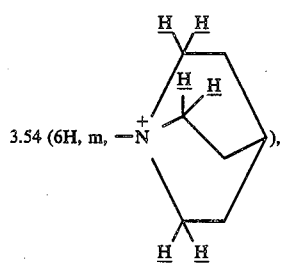), 4.04 (1H, dd, J=1.5 and 5.8 Hz, H$_6$)

4.22 and 4.94 (2H, each d, J = 13.8 Hz, CH$_2$—N 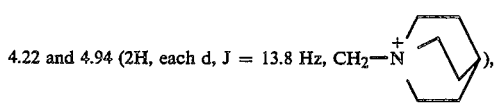), 5.77 (1H, d, J=1.5 Hz, H$_5$).
IR (KBr)=$\nu_{max}$ 1775, 1615, 1570 cm$^{-1}$
UV (H$_2$O)=$\lambda_{max}$ 253 ($\epsilon$=3,587), 317 nm ($\epsilon$=5,026).
(5R,6S)-6-[(1R)-hydroxyethyl]-2-(1-tropinio)-methylpenem-3-carboxylate(28);

(5R,6S)-6-[(1R)-hydroxyethyl]-2-[1-(5-oxo-5,6,7,8-tetrahydroquinolinio)]-methylpenem-3-carboxylate(29);
(5R,6S)-6-[(1R)-hydroxyethyl]-2-{5-[thieno(3,2-c)pyridinio]}-methylpenem-3-carboxylate(30);
(5R,6S)-6-[(1R)-hydroxyethyl]-2-{5-[thiazolo(4,5-c)pyridinio]}-methylpenem-3-carboxylate(31);
(5R,6S)-6-[(1R)-hydroxyethyl]-2-[1-(4-ethoxycarbonyl-1-methyl-piperazinio)]-methylpenem-3-carboxylate(32);
(5R,6S)-6-[(1R)-hydroxyethyl]-2-[1-(3,5-dimethyl-pyrazinio)]-methylpenem-3-carboxylate(33);
(5R,6S)-6-[(1R)-hydroxyethyl]-2-[1-(1-methyl-piperidinio)]-methylpenem-3-carboxylate(34);
NMR (200 MHz, D$_2$O)=$\delta$ppm 1.32 (3H, d, J = 6.4 Hz, C$\underline{H}_3$CH), 1.71 (2H, m, 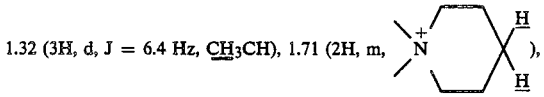), 1.93 (4H, m, 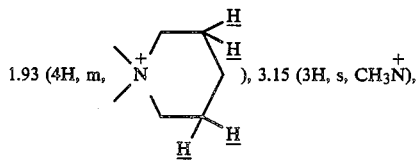), 3.15 (3H, s, CH$_3$N), 3.48 (4H, m, 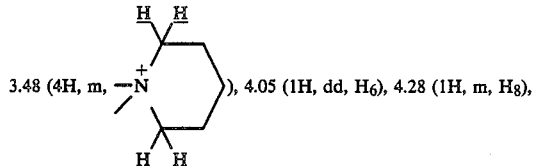), 4.05 (1H, dd, H$_6$), 4.28 (1H, m, H$_8$), 4.42 and 5.18 (2H, each d, J = 13.9 Hz, C$\underline{H}_2$—N 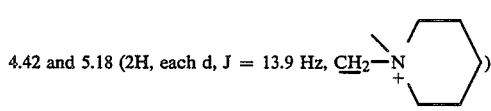), 5.78 (1H, d, H$_5$)

IR (KBr)=$\nu_{max}$ 1770, 1610, 1570 cm$^{-1}$
UV (H$_2$O)=$\lambda_{max}$ 210 ($\epsilon$=5,402), 253 ($\epsilon$=3,431), 318 nm ($\epsilon$=4,927).
(5R,6S)-6-[(1R)-hydroxyethy]-2-[1-(1,4-dimethyl-piperidinio)]-methylpenem-3-carboxylate(35);
(5R,6S)-6-[(1R)-hydroxyethyl]-2-[1-(2-methylpyrazolio)]-methylpenem-3-carboxylate(36);
(5R,6S)-6-[(1R)-hydroxyethyl]-2-(1-pyrazinio)-methylpenem-3-carboxylate(37);
(5R,6S)-6-[(1R)-hydroxyethyl]-2-[1-(3-methylpyrazinio)]-methylpenem-3-carboxylate(38);
(5R,6S)-[(1R)-hydroxyethyl]-2-{1-[1-(2-hydroxyethyl)-pyrrolidinio]}-methylpenem-3-carboxylate(39);
(5R,6S)-6-[(1R)-hydroxyethyl]-2-[3-(3-methyl-3-azoniabicyclo [3.2.2]nonane)]-methylpenem-3-carboxylate(40);
(5R,6S)-6-[(1R)-hydroxyethyl]-2-(1-quinolinio)-methyl-penem--3-carboxylate(41);
(5R,6S)-6-[(1R)-hydroxyethyl]-2-(2-isoquinolinio)-methylpenem-3-carboxylate(42); and
(5R,6S)-6-[(1R)-hydroxyethyl]-2-[1-(4-acetyl-1-methyl-piperazinio)]-methylpenem-3-carboxylate(43).

EXAMPLE 7

Operating as described in the previous examples, the following compounds were analogously prepared:

(5R,6S)-6-[(1R)-hydroxyethyl]-2-(N,N-dimethylanilinio)methylpenem-3-carboxylate

NMR (200 MHz, D$_2$O)=δppm 1.22 (3H, d, J=6.4 Hz, C$\underline{H}_3$CH), 3.69 and 3.73 (6H, each s, Me$_2$N$^+$), 3.83 (1H, dd, J=1.5 and 5.7 Hz, H$_6$), 4.17 (1H, m, H$_8$), 5.06 and 5.61 (2H, each d, J=13.7 Hz, C$\underline{H}_2$-N$^+$), 5.48 (1H, d, J=1.5 Hz, H$_5$), 7.6-7.8 (5H, m, Ar)

IR (KBr)=ν$_{max}$ 1775, 1615, 1565 cm$^{-1}$

UV (H$_2$O)=λ$_{max}$ 318 nm (ε=4,760);

(5R,6S)-6-[(1R)-hydroxyethyl]-2-(tributylammonio)methylpenem-3-carboxylate

NMR (200 MHz, D$_2$O)=δppm 0.95 (9H, t, J=7.3, —N$^+$(CH$_2$CH$_2$CH$_2$C$\underline{H}_3$)$_3$), 1.31 (3H, d, J=6.5 Hz, C$\underline{H}_3$CH), 1.38 (6H, m, —N$^+$(CH$_2$CH$_2$C$\underline{H}_2$CH$_3$)$_3$), 1.68 (6H, m, —N$^+$(CH$_2$C$\underline{H}_2$CH$_2$CH$_3$)+, 3.1-3.5 (6H, m, N$^+$(C$\underline{H}_2$CH$_2$CH$_2$CH$_3$)$_3$), 4.05 (1H, dd, H$_6$), 4.31 (1H, m, H$_8$), 5.78 (1H, d, H$_5$).

UV (H$_2$O)=λ$_{max}$ 255, 316 nm (4,900).

We claim:

1. A compound of the formula

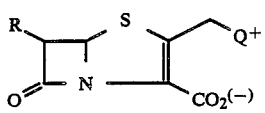

wherein R is a C$_1$-C$_3$ alkyl group substituted by a hydroxy group and Q$^+$ represents a group

wherein
(i) R$_1$, R$_2$ and R$_3$ are each independently a C$_1$-C$_4$ alkyl radical or
(ii) R$_1$ is C$_1$-C$_4$ alkyl unsubstituted or substituted by a cyano group and R$_2$, R$_3$ taken together with the nitrogen atom represent one of the heterocyclylammonium radicals

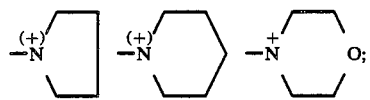

or (iii) R$_1$, R$_2$, R$_3$ taken together with the nitrogen atom represent one of the radicals

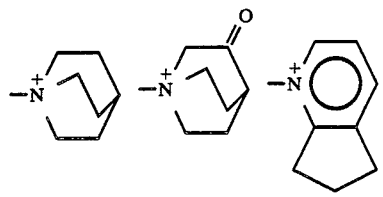

2. A compound of claim 1 wherein R is (alpha-hydroxy) ethyl and R$_1$ is methyl, ethyl or cyanomethyl.

3. A compound of claim 1 which is (5R,6S)-6[(1R)-hydroxyethyl]-2-triethylammonio-methyl-penem-3-carboxylate.

4. A compound of claim 1 which is ((5R,6S)-6-[(1R)-hydroxyethyl]-2-[1-(1-methylpyrooliinio)]-methyl-penem-3-carboxylate.

5. A compound of claim 1 which is (5R,6S)-6-[(1R)-hydroxyethyl]-2-[4-(4-methylmorpolinio)]-methyl-penem-3-carboxylate.

6. A compound of claim 1 which is (5R,6S) -6-[(1R)-hydroxyethyl]-2-[1-(1-cyanomethylpyrrolinio)]-methyl-penem-3-carboxylate.

7. A compound of claim 1 which is (5R,6S)-6-[(1R)-hydroxyethyl]-2-[1-(1-methylpiperidinio)]-methyl-penem-3-carboxylate.

8. A compound of claim 1 which is (5R,6S)-6-[(1R)-hydroxyethyl]-2-[1-(1-ethylpiperiodinio)]-methyl-penem-3-carboxylate.

9. A compound of claim 1 which is (5R,6S)-6-[(1R)-hydroxyethyl]-2-[1-(3-oxoquinuclidino)]-methylpenem-3-carboxylate.

10. A compound of claim 1 which is (5R,6S)-6-[(1R)-hydroxyethyl]-2-(1-quinuclidinio)-methyl-penem-3-carboxylate and.

11. A compound of claim 1 which is (5R,6S)-6-[(1R)-hydroxyethl]-2-[1-(6,7-dihydro-5$\underline{H}$-cyclopenta[b-]pyridinio]methylpenem-3-carboxylate.

12. An antibacterial pharmaceutical composition containing a pharmaceutically acceptable carrier and/or diluent and, as the active principle, an antibacterially effective amount of a compound of claim 1.

13. A method of producing an antibacterial effect in a patient in need of it, which comprises administering to said patient an antibaterially effective amount of a compound of claim 1.

14. A method of producing an antibacterial effect in a patient in need of it, said method comprising administering to said patient an antibacterially effective amount of a composition of claim 12.

* * * * *